United States Patent
Eckman et al.

(10) Patent No.: US 6,649,196 B2
(45) Date of Patent: Nov. 18, 2003

(54) METHODS OF REDUCING β-AMYLOID POLYPEPTIDES

(75) Inventors: Christopher B. Eckman, Ponte Vedra Beach, FL (US); Debra Yager, Jacksonville, FL (US); Sharie Haugabook, Jacksonville, FL (US); Abdul Fauq, Jacksonville, FL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 09/804,420

(22) Filed: Mar. 12, 2001

(65) Prior Publication Data

US 2002/0127290 A1 Sep. 12, 2002

(51) Int. Cl.⁷ .............................................. A61K 35/78
(52) U.S. Cl. ...................................... 424/773; 424/725
(58) Field of Search ................................. 424/725, 773

(56) References Cited

U.S. PATENT DOCUMENTS

| | | |
|---|---|---|
| 4,666,829 A | 5/1987 | Glenner et al. |
| 5,538,845 A | 7/1996 | Knops et al. |
| 5,552,426 A | 9/1996 | Lunn et al. |
| 5,604,102 A | 2/1997 | McConlogue et al. |
| 5,703,129 A | 12/1997 | Felsenstein et al. |
| 5,766,846 A | 6/1998 | Schlossmacher et al. |
| 6,096,782 A | 8/2000 | Audia et al. |
| 6,191,166 B1 | 2/2001 | Audia et al. |
| 6,211,235 B1 | 4/2001 | Wu et al. |

FOREIGN PATENT DOCUMENTS

| | | | |
|---|---|---|---|
| JP | 59020298 A | 2/1984 | |
| KR | 9300059 B | 1/1993 | |

OTHER PUBLICATIONS

Asami–Odaka et al., "Long Amyloid β–Protein Secreted from Wild–Type Human Neuroblastoma IMR–32 Cells," *Biochem.*, 1995, 34:10272–10278.

Brinker, "Variations in Effective Botanical Products—The Case for Diversity of Forms for Herbal Preparations as Supported by Scientific Studies," *HerbalGram*, 1999, 46:36–50.

Buxbaum et al., "Processing of Alzheimer β/A4 amyloid precursor protein: Modulation by agents that regulate protein phosphorylation," *Proc. Natl. Acad. Sci. USA*, 1990, 87:6003–6006.

Buxbaum et al., "Protein phosphorylation inhibits production of Alzheimer amyloid β/A4 peptide," *Proc. Natl. Acad. Sci. USA*, 1993, 90:9195–9198.

Chevallier et al., "Cathepsin D displays in vitro β–secretase–like specificity," *Brain Res.*, 1997, 750:11–19.

Dovey et al., "Functional gamma–secretase inhibitors reduce beta–amyloid peptide levels in brain," *J. Neurochem.*, 2001, 76:173–181.

Eckman et al., "Degradation of the Alzheimer's Amyloid β Peptide by endothelin–converting Enzyme," *J. Biol. Chem.*, 2001, 276(27):24540–24548.

Fassbender et al., "Simvastatin strongly reduces levels of Alzheimer's disease β–amyloid peptides Aβ42 and Aβ40 *in vitro* and *in vivo*," *Proc. Natl. Acad. Sci. USA*, 2001, 98(10):5856–5861.

Frears et al., "The role of cholesterol in the biosynthesis of β–amyloid," *NeuroReport*, 1999, 10(8):1699–1705.

Gandy, "Neurohormonal Signaling Pathways and the Regulation of Alzheimer β–Amyloid Precursor Metabolism," *Trends Endocrinol. Metab.*, 1999, 10(7):273–279.

Gouras et al., "Testosterone reduces neuronal secretion of Alzheimer's β–amyloid peptides," *Proc. Natl. Acad. Sci. USA*, 2000, 97(3):1202–1205.

Haass and Selkoe, "Cellular Processing of β–Amyloid Precursor Protein and the Genesis of Amyloid β–Peptide," *Cell*, 1993, 75:1039–1042.

Haass et al., "Normal Cellular Processing of the β–Amyloid Precursor Protein Results in the Secretion of the Amyloid β Peptide and Related Molecules," *Ann. N.Y. Acad. Sci.*, 695:109–116 1993.

Haugabook et al., "Reduction of Aβ accumulation in the Tg2576 animal model of Alzheimer's disease after oral administraction of the phosphatidyl–inositol kinase inhibitor wortmannin," *FASEB J.*, 2001, 15:16–18.

Holcomb et al., "Accelerated Alzheimer–type phenotype in transgenic mice carrying both mutant *amyloid precursor protein* and *presenilin 1* transgenes," *Nature Med.*, 1998, 4:97–100.

Hung et al., "Activation of Protein Kinase C Inhibits Cellular Prodution of the Amyloid β–Protein," *J. Biol. Chem.*, 1993, 268(31):22959–22962.

Iversen et al., "The toxicity *in vitro* of β–amyloid protein," *Biochem. J.*, 1995, 311:1–16.

Jacobsen et al., "The Release of Alzheimer's Disease β Amyloid Peptide is Reduced by Phorbol Treatment," *J. Biol. Chem.*, 1994, 269(11):8376–8382.

Koo, "Phorbol Esters Affect Multiple Steps in β–Amyloid Precursor Protein Trafficking and Amyloid β–Protein Production," *Mol. Med.*, 1997, 3(3):204–211.

Lahiri et al., "The secretion of amyloid β–peptides is inhibited in the tacrine–treated human neuroblastoma cells," *Mol. Brain Res.*, 1998, 62:131–140.

(List continued on next page.)

Primary Examiner—Leon B. Lankford, Jr.
Assistant Examiner—Susan D. Coe
(74) Attorney, Agent, or Firm—Fish & Richardson P.C., P.A.

(57) ABSTRACT

The invention features methods of reducing the level of a β-amyloid (Aβ) polypeptide using an Cimicifuga extract. The invention also features methods of producing an active fraction from an extract of Cimicifuga. The invention further features a composition containing an active fraction of a Cimicifuga extract and an article of manufacture containing such a composition.

23 Claims, No Drawings

OTHER PUBLICATIONS

Lahiri et al., "Cholinesterase inhibitors, β–amyloid precursor protein and amyloid β–peptides in Alzheimer's disease," *Acta Neurol. Scand.*, 2000, Suppl. 176:60–67.

Lieberman, "Evidence–Based Natural Medicine—A Review of the Effectiveness of *Cimicifuga racemosa* (Black Cohosh) for the Symptoms of Menopause," *J. Women's Health*, 1998, 7(5):525–529.

Lim et al., "Ibuprofen Suppresses Plaque Pathology and Inflammation in a Mouse Model for Alzheimer's Disease," *J. Neurosci.*, 2000, 20(15):5709–5714.

Masters et al., "Amyloid plaque core protein in Alzheimer disease and Down syndrome," *Proc. Natl. Acad. Sci. USA*, 1985, 82:4245–4249.

Murray, "Indigestion, antacids, achlorydria and H. pylori," *Am. J. Nat. Med.*, 1997, 4:11–14, 16–17.

Nitsch et al., "The Selective Muscarinic M1 Agonist AF102B Decreases Levels of Total Aβ in Cerebrospinal Fluid of Patients with Alzheimer's Disease," *Ann. Neurol.*, 2000, 48:913–918.

Ohyagi et al., "Selective increase in cellular Aβ42 is related to apoptosis but not necrosis," *NeuroReport.*, 2000, 11:167–171.

Petanceska and Gandy, "The Phosphatidylinositol 3–Kinase Inhibitor Wortmannin Alters the Metabolism of the Alzheimer's Amyloid Precursor Protein, " *J. Neurochem.*, 1999, 73:2316–2320.

Querfurth and Selkoe, "Calcium Ionophore Increases Amyloid β Peptide Production by Cultured Cells," *Biochem.*, 1994, 33(15):4550–4561.

Querfurth et al., "Caffeine Stimulates Amyloid β–Peptide Release from β–Amyloid Precursor Protein–Transfected HEK293 Cells," *J. Neurochem.*, 1997, 69:1580–1591.

Racchi and Govoni, "Rationalizing a pharmacological intervention on the amyloid precursor protein metabolism," *Trends Pharmacol. Sci.*, 1999, 20:418–423.

Sambamurti et al., "Glycosylphosphatidylinositol–anchored Proteins Play an Important Role in the Biogenesis of the Alzheimer's Amyloid β–Protein," *J. Biol. Chem.*, 1999, 274(38):26810–26814.

Savage et al., "Turnover of Amyloid β–Protein in Mouse Brain and Acute Reduction of Its Level by Phorbol Ester," *J. Neurosci.*, 1998, 18(5):1743–1752.

Shoji et al., "Production of the Alzheimer Amyloid β Protein by Normal Proteolytic Processing," *Science*, 1992, 258:126–129.

Suzuki et al., "An Increased Percentage of Long Amyloid β Protein Secreted by Familial Amyloid β Protein Precursor (βAPP$_{717}$) Mutants," *Science*, 1994, 264:1336–1340.

Xu et al., "Estrogen reduces neuronal generation of Alzheimer β–amyloid peptides," *Nat. Med.*, 1998, 4(4):447–451.

METHODS OF REDUCING β-AMYLOID POLYPEPTIDES

TECHNICAL FIELD

This invention relates to β-amyloid (Aβ) polypeptides, and more particularly to methods of reducing Aβ polypeptides using an extract, or active fraction thereof, of Cimicifuga.

BACKGROUND

Patients with Alzheimer's disease (AD) are typically presented to a clinician by a relative who has observed a decline in memory with or without a change in other cognitive abilities such as declines in executive function, difficulty in word finding or visuo-spatial impairment such as an inability to draw complex geometric structures or becoming lost in familiar places. Neuropathological analysis of brains from patients with AD has revealed extensive neuronal and synaptic loss in select brain regions, neurofibrillary tangles, and the deposition of β-amyloid (Aβ) polypeptides in the form of senile plaques throughout the hippocampus and neocortex.

Aβ polypeptides are produced from the amyloid precursor protein (APP) through the combined proteolytic actions of β- and γ-secretases and are then secreted into the extracellular milieu. Biochemical and immunocytochemical studies have revealed that the Aβ polypeptides deposited in brains from patients with AD have substantial amino- and carboxyl-terminal heterogeneity and can contain from 39 to 43 amino acid residues, with β-amyloid 1-40 (Aβ40) and 1-42 (Aβ42) being the most predominant. By comparing signals obtained using antibodies directed at the amino terminus of Aβ with those obtained by capturing the peptide from an internal epitope, it was found that virtually all Aβ42 in AD brain is amino-terminally modified and/or truncated.

SUMMARY

The invention features methods of reducing the level of an Aβ polypeptide using a Cimicifuga extract. The invention also features methods of producing an active fraction from an extract of Cimicifuga. An active fraction is one that is able to reduce the level of an Aβ polypeptide in or secreted from a cell (in vitro or in vivo). The invention further features a composition containing an active fraction of a Cimicifuga extract and an article of manufacture containing such a composition.

In one aspect, the invention provides methods of reducing the level of a β-amyloid (Aβ) polypeptide in or secreted from a cell. The methods include contacting the cell with an amount of a Cimicifuga extract or of an active fraction thereof in an amount that is effective for reducing the level of the Aβ polypeptide and monitoring the level of the Aβ polypeptide in or secreted from the cell. Representative cells include H4 cells, M17 cells, 293 cells, Chinese hamster ovary (CHO) cells, primary fibroblasts, C6, primary neuronal, primary mixed brain cultures, Daoy, SK-N-SH, SK-N-AS and SK-N-FI.

In another aspect, the invention provides methods for reducing the level of an Aβ polypeptide in a mammal, including administering an amount of a Cimicifuga extract or an active fraction thereof to the mammal in an amount that is effective for reducing the level of the Aβ polypeptide and monitoring the level of the Aβ polypeptide in the mammal.

In another aspect of the invention, there are provided methods of treating a mammal having AD or at risk to develop AD. The methods include administering an amount of a Cimicifuga extract or an active fraction thereof to the mammal in an amount that is effective for treating or preventing AD. Generally, the extract or active fraction thereof is administered to a mammal orally, intravenously, intracranially, intracerebrally, subcutaneously, intramuscularly, intranasally or intraperitoneally. A representative mammal is a rodent, for example, a mouse. In one embodiment, the mouse expresses an APP carrying a Swedish mutation. An example of such a mouse is a Tg2576 mouse.

The Cimicifuga extract or active fraction thereof can be from C. racemosa, and further can be obtained from the root or rhizome of a C. racemosa plant. The C. racemosa extract is generally an ethanolic or an aqueous extract. An active component within an active fraction can be soluble in a solvent such as methylene dichloride, ethyl acetate and n-butanol, and active components soluble in such solvents are typically lipophilic. An active component within an active fraction that is capable of reducing the level of an Aβ polypeptide can have a molecular weight of less than 10 kD.

A reduction in the level of an Aβ polypeptide can be due to decreased production of the Aβ polypeptide or increased catabolism of the Aβ polypeptide. In an embodiment of the invention, the level of the Aβ polypeptide is reduced by at least 10%, at least 25%, at least 50%, or at least 80% compared to the level of the Aβ polypeptide in or secreted from a corresponding cell not contacted with the extract or active fraction thereof. A reduction in the level of an Aβ polypeptide can be a reduction in the level of Aβ40 or Aβ42. Further, the reduction in the level of an Aβ polypeptide can be a preferential reduction in the level of Aβ42. In addition, the extract or active fraction thereof typically should have no significant effect on the level of one or more of APP, CTFα, CTFβ, or sAPPα.

In yet another aspect of the invention, there are provided methods of producing an active fraction of a Cimicifuga extract that reduces the level of an Aβ polypeptide upon contact with a cell. The methods include obtaining an extract of Cimicifuga plant material, size-fractionating the extract through a filter to obtain an active fraction, and testing the active fraction to confirm that the active fraction reduces the level of an Aβ polypeptide. Generally, an active fraction contains active components having a molecular weight of less than about 10 kD.

The invention also provides methods of producing an active fraction of a Cimicifuga extract that reduces the level of an Aβ polypeptide upon contact with a cell, including obtaining an extract of Cimicifuga plant material, extracting the Cimicifuga extract with hexane (thereby producing a hexane-soluble fraction and a hexane-insoluble fraction) and testing the hexane-insoluble fraction to confirm that the hexane-insoluble fraction reduces the level of the Aβ polypeptide. A representative hexane is n-hexane. Such methods can additionally include extracting the hexane-insoluble fraction with a dichloroalkane (producing a dichloroalkane-soluble fraction and a dichloroalkane-insoluble fraction) where the dichloroalkane-soluble fraction typically reduces the level of the Aβ polypeptide upon contact with a cell. A representative dichloroalkane is methylene dichloride. Methods of producing an active fraction also can include extracting the dichloroalkane-soluble fraction with an alkylacetate (producing an alkylacetate-soluble fraction and an alkylacetate-insoluble fraction) where the alkylacetate-soluble fraction typically reduces the level of an Aβ polypeptide. A representative alkylacetate is ethyl acetate. Further, methods of the invention can include extracting the alkylacetate-soluble fraction with an alcohol (producing an alcohol-soluble fraction and an alcohol-insoluble fraction) wherein the alcohol-soluble fraction typically reduces the level of the Aβ polypeptide. A representative alcohol is n-butanol. The product of any of the above-described extractions or fractionations can be further concentrated, for example, by lyophilizing.

In another aspect of the invention, there is provided a composition containing an active fraction of a Cimicifuga extract and a pharmaceutically acceptable carrier. Such an active fraction can reduce the level of an Aβ polypeptide upon contact with a cell producing the Aβ polypeptide.

In still yet another aspect of the invention, there is provided an article of manufacture containing an active fraction of a Cimicifuga extract, a pharmaceutically acceptable carrier, and packaging material. Generally, packaging material contains a label or package insert indicating that the composition is effective for reducing the level of an Aβ polypeptide.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DETAILED DESCRIPTION

The invention provides methods of reducing the level of an Aβ polypeptide in or secreted from a cell. Methods of the invention include contacting a cell with an extract of Cimicifuga or an active fraction thereof in an effective amount such that Aβ is reduced, and subsequently monitoring the level of Aβ.

Traditional Chinese medicine has long employed Cimicifuga species for the treatment of menstrual cramps, fatigue, anxiety, rheumatoid arthritis, alleviation of fever, pain, inflammation, sedation, swelling of joints, respiratory congestion from colds, and high blood pressure. More than two centuries ago, Native Americans were using the root of *Cimicifuga racemosa,* also known as black cohosh, black snakeroot, bugbane, bugwort, and squawroot, to relieve many of the symptoms associated with menstruation and menopause, including cramps, hot flashes, headaches, irritability, sweats, as well as many of the symptoms unrelated to menstruation discussed above. Cimicifuga, a perennial native woodland plant, includes several commonly known species that are used medicinally and/or ornamentally (e.g., *C. simplex, C. dahurica, C. foetida, C. japonica, C. acerina,* and *C. racemosa*). Extracts or active fractions of *C. racemosa* are particularly useful in the methods of the invention.

Cimicifuga Extracts and Reduction of Aβ Polypeptide Levels

The invention features methods of reducing the level of an Aβ polypeptide in or secreted from a cell. As used herein, an Aβ polypeptide refers to a portion of an APP (e.g., human APP) that is produced following cleavage by β-secretase and γ-secretase (for example, residues 671-711 (Aβ40) or 671-713 (Aβ42) of GenBank Accession No. D87675). An Aβ polypeptide can have from 39 to 43 amino acid residues (e.g., 39, 40, 41, 42 or 43 residues). Given the heterogeneity in the length of Aβ polypeptides, it is a further feature of the invention that an extract can reduce the level of a specific Aβ polypeptide (e.g., Aβ40 or Aβ42). The ability to distinguish a reduction in the level of, for example, Aβ40 or Aβ42 is significant, since Aβ42 is considered to be more amyloidogenic. For example, immunocytochemical analysis has shown immunolabeling for Aβ42 in all types of senile plaques, poor labeling of plaques using Aβ40 end-specific antibodies, and detection of both the Aβ40 and Aβ42 epitopes in cerebrovascular amyloid. Moreover, analysis of familial AD (FAD)-linked mutations has shown elevations in extracellular Aβ accumulation, particularly Aβ42. As described herein, the reduction of Aβ polypeptides by Cimicifuga extracts can be preferential for Aβ42. As used herein "preferential" refers to a significant reduction of one Aβ polypeptide (e.g., Aβ42) compared to the level of one or more different Aβ polypeptides (e.g., Aβ40). "Significant" refers to a statistical calculation of significance in which a p-value of less than 0.05 (e.g., a p-value of less than 0.025 or less than 0.01) is obtained using an appropriate statistical calculation, e.g., a paired t-test. Therefore, a p-value of greater than 0.05 indicates a lack of statistical significance based on such a calculation.

Methods of the invention include contacting a cell (in vitro or in vivo) with an effective amount of a Cimicifuga extract or active fraction thereof and monitoring the level of Aβ in or secreted from the cell. An effective amount of an extract or an active fraction is an amount that reduces the level of an Aβ polypeptide in or secreted from a cell by at least 10% (e.g., at least 20%, 25%, 30%, 40%, 50%, 60%, 70%, 80%, or 90%) or completely abolishes the level of an Aβ polypeptide compared to the level of the Aβ polypeptide in or secreted from a corresponding cell not treated with the extract or active fraction. A component in an active fraction that reduces the level of an Aβ polypeptide can exert an effect at any of a number of steps along the pathway of Aβ secretion and, in the case of AD, deposition in the brain. The level of Aβ polypeptide not only depends upon its production, but also on the mechanisms responsible for its removal. Without being bound by a particular mechanism, a reduction in the level of an Aβ polypeptide can be due to the activity of binding proteins that sequester the polypeptide, or to other cellular mechanisms such as decreased production or increased catabolism of an Aβ polypeptide. By way of example, catabolism of an Aβ polypeptide likely involves both intracellular (e.g., acting at the site of Aβ polypeptide generation and/or within the secretory pathway) and extracellular (e.g., cell-surface, secreted, endosomal and/or lysosomal) proteases. Compounds that reduce the level of one or more Aβ polypeptides can be useful, for example, as therapeutic compounds or to design therapeutic compounds.

Cells can be contacted in vitro with a Cimicifuga extract or active fraction thereof while in cell culture (e.g., introducing an extract into culture media). Representative cells that can be used include, but are not limited to, H4 neuroglioma, M17 neuroblastoma, human kidney 293, Chinese hamster ovary (CHO), primary fibroblast, C6, primary neuronal, primary mixed brain, Daoy, SK-N-SH, SK-N-AS and SK-N-FI-cells. Cells suitable for primary screening can be obtained from the American Type Culture Collection (ATCC) (10801 University Blvd., Manassas, Va. 20110). In addition, such cells can be transgenic cells carrying a construct containing a nucleic acid encoding APP or any portion of APP containing an Aβ fragment. For example, H4βAPP695wt cells are H4 cells carrying a human wild-type 695-amino acid APP isoform. Isoforms of APP that are produced by alternate mRNA splicing include the aforementioned APP695 as well as APP751 and APP770. In addition, cells can express human APP carrying a mutation that, for example, changes a lysine-methionine at amino acid residues 670 and 671 to an asparagine-leucine (i.e., the Swedish mutation) or one that changes a valine to an isoleucine at amino acid residue 717.

A Cimicifuga extract or active fraction therefrom also can be administered to a mammal such as a human or a rodent to reduce the level of Aβ. For example, a Cimicifuga extract can be administered to an individual over the age of 60, or to an individual diagnosed with AD or that is at risk for developing AD (e.g., based upon familial history or the presence of a mutation associated with AD). A Cimicifuga extract also can be administered to a rodent such as a guinea pig or a mouse, and in particular, to an animal model of AD. Animal models of AD are available that accumulate Aβ and that develop plaques in an age-dependent manner. In particular, transgenic mice are available that carry a mutation in a presenilin gene and/or express an APP carrying a mutation (for example, a Swedish mutation). A representative mouse carrying a Swedish mutation is Tg2576 (Holcomb et al., 1998, *Nat. Med.,* 4:97–100). The Tg2576 mouse accumulates Aβ polypeptides and develops plaques in an age-dependent manner. A Cimicifuga extract or active fraction thereof can be administered to a mammal by any route, including orally, intravenously, intracranially, intracerebrally, subcutaneously, intramuscularly, intranasally or intraperitoneally.

Since a reduction in the level of an Aβ polypeptide in vitro or in vivo can be a direct result of a decrease in cell viability, toxic effects of a Cimicifuga extract or active fraction thereof on a cell or a mammal are typically evaluated. Methods to evaluate cellular toxicity are known to those of skill in the art. For example, the degree of conversion of a tetrazolium salt (e.g., MTS) into formazan is directly proportional to the number of metabolically active cells on a cell culture plate. Conversion of MTS can be measured using the CellTiter 96® assay kit (Promega; Madison, Wis.). Further, the number of lysed cells is quantitatively proportional to the LDH (lactate dehydrogenase)-catalyzed conversion of tetrazolium salt to red formazan. The Cytotox 96 assay kit (Promega) can be used to examine LDH release.

To address issues of toxicity in vivo, standard haematoxylin/eosin (H/E) staining can be performed on the liver, kidney, spleen, and brain of an animal (e.g., a rodent such as an animal model of AD) to look for any abnormalities apparent between the extract-treated and control groups. In addition, serum levels of blood urea nitrogen (BUN), aspartate amino transaminase (AST-SGOT), and alkaline phosphatase (ALP) can be monitored in an animal to evaluate renal function, liver damage, and drug-induced biliary obstructions.

Methods of Detecting Aβ Polypeptides

Methods for detecting Aβ in cell culture or in a biological sample from an individual (e.g., plasma or cerebrospinal fluid) are known to those of skill in the art. High throughput screens have been developed to examine the level of Aβ40 or Aβ42 in medium conditioned by a cell line over time. A highly specific sandwich ELISA is described herein using a BAN-50 antibody, which specifically captures Aβ at the N-terminus, and then either a BA-27 antibody, which detects only full-length Aβ polypeptides ending at position 40, or a BC-05 antibody, which detects only full-length Aβ polypeptides ending at position 42 (Suzuki et al., 1994, Science, 264:1336–40; Asami-Odaka et al., 1995, Biochem., 34:10272–8).

Suitable antibodies that detect an epitope within Aβ (or within the Aβ portion of APP) are also commercially available from a variety of sources, including, but not limited to, Biosource International (Camarillo, Calif.), Senetek PLC (London, England), Zymed Laboratories (San Francisco, Calif.), Peninsula Laboratories (San Carlos, Calif.) and Boehringer Mannheim (Indianapolis, Ind.). Several of the commercial sources listed herein also provide antibodies with specific binding affinity for either Aβ40 or Aβ42. In addition, BNT-77 is an antibody that captures rodent Aβ (Asami-Odaka et al., 1995, Biochem., 34:10272–8) that can be used in conjunction with the BA-27 or BC-05 antibodies described above, In addition to the specific sandwich ELISA described herein, other types of solid phase immunoassays as well as immunoassay formats such as Western blots or immunoprecipitations may be used to detect Aβ and are well known in the art. See, *Short Protocols in Molecular Biology,* Ch. 11, John Wiley & Sons, Ed., Ausubel et al., 1992. Solid-phase immunoassays include competition immunoassays, immobilized-antigen immunoassays, immobilized-antibody immunoassays, and double-antibody immunoassays. For example, a typical double-antibody immunoassay to detect Aβ can include the following steps: attaching an antibody with binding affinity for Aβ to a solid support; exposing the antibody to unlabeled Aβ polypeptide; washing to remove unbound Aβ; and quantitating the amount of Aβ bound to the immobilized antibody using an excess of a second antibody. The second antibody can have binding affinity for Aβ and can be radiolabeled or conjugated to a chemical or enzyme for detection following addition of an appropriate substrate.

Western blotting to detect Aβ typically includes the steps of electrophoretically separating peptides in or secreted from a cell; transferring the peptides from the separation medium (e.g., a gel) to a solid support (e.g., nitrocellulose, nylon); and probing with antibodies with binding affinity for Aβ. Probing can be direct (e.g., a labeled primary antibody) or indirect (e.g., an unlabeled antibody specific for Aβ, which is subsequently detected with a labeled secondary antibody or immunological reagent, for example, protein A or anti-immunoglobulin).

Aβ immunoprecipitation methods generally include the following steps: radiolabeling cells expressing Aβ; lysing the cells; forming specific immune complexes between Aβ and an antibody with binding affinity for Aβ; collecting and purifying the immune complexes; and analyzing the radiolabeled Aβ in the immunoprecipitate. Immunoprecipitation is often used to detect and quantitate target antigens in complex mixtures of proteins. Immunoprecipitation can be used to analyze unlabeled proteins from unlabeled cells, provided sufficiently sensitive methods are available to detect the target protein after it has been dissociated from the antibody.

A detectable label, e.g., a radioactive label (e.g., $^3H$, $^{125}I$, $^{131}I$, $^{32}P$, $^{35}S$, and $^{14}C$) or a non-radioactive label (e.g., a fluorescent label, a chemiluminescent label, a paramagnetic label, or an enzyme label) may be attached to an antibody or a fragment thereof using techniques known to those of ordinary skill in the art. Examples of enzyme labels used routinely in the art for detection and quantitation include horseradish peroxidase (HRP) and alkaline phosphatase (AP). The substrates available for either HRP or AP labels are known in the art and can be selected based upon the desired method of detecting complex formation (e.g., a fluorogenic, chemiluminescent or calorimetric signal).

Aβ that has been detected by any of the methods described herein or other methods known to those of skill in the art can be visualized or quantitated using methods routine in the art, including autoradiography of a radioactive label (e.g., x-ray film, phosphorimaging, or densitometric analysis) and spectrophotometry of a fluorescent label or of a calorimetric reaction produced by, for example, an enzymatic label. In addition, a non-Aβ polypeptide also can be detected and quantitated using methods similar to those described herein for Aβ (e.g., for normalization purposes).

In addition, mass spectrometry (MS) can be used to detect and quantitate Aβ polypeptides. Several types of MS are available and routinely used in the art, and include Fourier-transform MS, Ion-trap MS, Magnetic-sector MS, Quadropole MS and Time-of-flight (TOF) MS. By way of example, Ciphergen (Fremont, Calif.) sells a biochip system for capturing Aβ polypeptides from culture medium or a biological sample and utilizes SELDI technology (Surface-Enhanced Laser Desorption/Ionization) with TOF-MS to detect and quantitate the level of Aβ polypeptides.

Neuritic plaques in the brain of an individual with AD can be detected and/or monitored in vivo using an Aβ polypeptide covalently modified with a polyamine (e.g., putrescine, spermidine, or spermine) (Wengenack et al., 2000, *Nat Biotechnol.*, 18:868–72). A radiolabeled polyamine-modified Aβ polypeptide can be administered to an individual intravenously and detected using standard methods. For example, a radiolabel suitable for diagnostic imaging can be used (e.g., $^{123}$I) and detected using single photon emission computed tomography (SPECT).

Producing Cimicifuga Extracts and Active Fractions Thereof

Extraction is a process whereby the desired constituents of a plant or plant part are removed using a solvent or other means. Generally, an extract of Cimicifuga is obtained from the root or rhizome of the plant, although leaves, stems and flowers also can be used. The Cimicifuga extract or active fraction can be from *C. racemosa*. To produce an extract, plant material is usually first cleaned and dried if necessary. Drying can be done naturally (e.g., by air drying) or artificially (e.g., using warm-air fans or conveyor dryers). The plant material then can be ground, cut, or shredded using, for example, hammer action, pressure, friction or impact cutting. Methods of removing the desired constituents from the plant material include, but are not limited to, organic solvent extraction, supercritical gas extraction, and steam distillation. By way of example, there are a number of procedures for organic solvent extraction, including maceration (soaking and agitating the plant material with a solvent), percolation (repeated rinsing of the plant material with a solvent), and countercurrent extraction (continuous flow of a solvent in the opposite direction as the plant material). Representative solvents include, but are not limited to, ethanol, benzene, toluene and ether. Aqueous extracts, such as decoctions (boiling the plant material, generally used for hard tissues), infusions (steeping the plant material, generally used for soft tissues) or macerations, can also be produced, although microbial contamination can be a concern with aqueous extraction methods. As used herein in the methods of the invention, a *C. racemosa* extract can be an ethanolic extract or an aqueous extract, depending upon the solubility of an active component that reduces the level of an Aβ polypeptide. Extracts of Cimicifuga are commercially available, and include Remifemin® (SmithKline Beecham, Research Triangle Park, N.C.), and Black Cohosh (Viable Herbal Solutions, Morrisville, Penn.; or Whole Health Discount Center, http://www.WholeHealthDiscountCenter.com).

Methods of producing active fractions (i.e., containing one or more active components) from a Cimicifuga extract are provided by the invention. Active components of a Cimicifuga extract or active fraction can include, but are not limited to, polyphenols, flavonoids, aromatic acids, metabolites, alkaloids, proteins, carbohydrates, starches, steroids, resins, elements or combinations thereof (e.g., glycoproteins) that, alone or in combination with other components, can reduce the level of an Aβ polypeptide. For example, fractionating by traditional solvent extraction employs partitioning of a solute between two immiscible phases, typically an organic phase (e.g., n-hexane, methylene dichloride, ethyl acetate or n-butanol) and an aqueous phase. Rapid extraction kinetics and the ability to utilize a number of different diluents, extractants, and aqueous phases makes solvent extraction a powerful separation method. In addition, numerous other separation procedures can be employed to further purify desired components or remove unwanted or contaminating components, including decanting, filtration, sedimentation, centrifugation, heating, adsorption, precipitation, chromatography, or ion exchange. The resulting active fraction can be subsequently concentrated by evaporation, vaporization, lyophilization or vacuum drying. Although the invention exemplifies fractionating using organic solvent partitioning, those of skill in the art are aware of the advantages of using certain separation techniques in combination with others to increasingly partition one or more active components into active fractions.

One method of the invention includes obtaining an extract of Cimicifuga plant material and size-fractionating the extract, e.g., through a filter. The flow-through represents an active fraction. Using this or a similar method of fractionating a Cimicifuga extract, an active component within the active fraction can pass through a 10 kilodalton (kD) nominal molecular weight filter or concentrator.

Another method of producing an active fraction of a Cimicifuga extract includes obtaining an extract of Cimicifuga plant material, and extracting the extract with hexane (e.g., n-hexane). The hexane-insoluble fraction can be used to reduce the level of an Aβ polypeptide following contact with a cell or can be further fractionated. For example, the hexane-insoluble fraction can be extracted with a dichloroalkane (e.g., methylene dichloride or dichloroethane). As described herein, the dichloroalkane-soluble fraction is able to reduce levels of Aβ. An active component within the dichloroalkane-soluble fraction can be further partitioned by extracting with an alkylacetate (e.g., ethyl acetate or methyl acetate) and obtaining an alkylacetate-soluble fraction. An active component within the alkylacetate-soluble fraction can be further partitioned by extracting with an alcohol solvent (e.g., n-butanol or 1-pentanol) and obtaining the alcohol-soluble fraction. Those of skill in the art are aware of additional steps during fractionating that can facilitate sample handling (e.g., concentrating an active fraction).

Given the high throughput cell based assays described herein, hundreds or thousands of fractions or combinations of fractions can be rapidly screened to identify those containing one or more active components or to identify fractions that, when combined, confer activity. An animal such as the Tg2576 mouse or a transgenic mouse carrying a Swedish mutation and a mutation in a presenilin sequence also can be used to evaluate the level of Aβ (e.g., in plasma or homogenized brain using, for example, the sandwich ELISA described herein), plaque burden (e.g., in brain tissue using, for example, immunocytochemical analysis), behavior/memory (e.g., using a Morris water maze to evaluate spatial reference memory), or other neurological markers such as differences in astroglia, dystrophic neuritis, microglia and the state of tau phosphorylation (e.g., by immunocytochemical analysis of brain tissue) following administration of a Cimicifuga extract or active fraction.

An active component from a Cimicifuga extract or active fraction that is able to reduce Aβ levels can be soluble in methylene dichloride, ethyl acetate and n-butanol, generally indicating a lipophilic active component. Lipophilic compounds are those that prefer a nonpolar environment to an aqueous one. Compounds from C. racemosa extract have been identified previously using methods such as those described herein, and include a phytoestrogen capable of binding estrogen receptors, and cimicifugin and macrotin resins, which effect, among others, the reproductive and nervous systems. Also identified from Cimicifuga extracts are triterpene glycosides, including cimicifugoside, which is believed to affect the hypothalamus-pituitary system and the reproductive and nervous systems, actein, a steroidal derivative that lowers blood pressure in animals, 27-deoxyactein, and racemoside. An isoflavone called formonenetin has been identified as binding to estrogen receptors in the rat uterus. Aromatic acids, including ferulic acid and isoferulic acid are believed responsible for the extract's anti-inflammatory effects.

Compositions and Articles of Manufacture

The invention further features a composition containing an active fraction of a Cimicifuga extract. A composition containing an active fraction of a Cimicifuga extract can be in any form provided the composition can be placed in contact with a cell in an amount and for a length of time effective to reduce the level of an Aβ polypeptide.

Compositions of the invention may be administered on a continuous or an intermittent basis. By way of example, a composition within the scope of the invention can be in the form of a liquid, solution, suspension, pill, capsule, tablet, gelcap, powder, gel, ointment, cream, nebulae, mist, atomized vapor, or aerosol. For the purpose of this invention, routes of administration include, but are not limited to, oral, nasal, intravenous, intramuscular, intraperitoneal, subcutaneous, intrathecal, intradermal, or topical. The route of administration can depend on a variety of factors, such as the environment in which cells are contacted and therapeutic goals. The dosages of a particular composition will depend on many factors, including the mode of administration and the cells being treated. Typically, the amount of an active fraction contained within a single dose of a composition will be an amount that effectively reduces the level of an Aβ polypeptide without inducing significant toxicity.

In addition, compositions within the scope of the invention can contain a pharmaceutically acceptable carrier for in vivo administration to a mammal, including, without limitation, sterile aqueous or non-aqueous solutions, suspensions, and emulsions. Examples of non-aqueous solvents include, without limitation, propylene glycol, polyethylene glycol, vegetable oils, and injectable organic esters. Aqueous carriers include water, alcohol, saline, and buffered solutions. Pharmaceutically acceptable carriers can also include physiologically acceptable aqueous vehicles (e.g., physiological saline or artificial cerebral-spinal fluid) or other known carriers appropriate to specific routes of administration. Additional compounds can be included in a composition, such as steroids, mucolytic agents, anti-inflammatory agents, immunosuppressants, dilators, vasoconstrictors, or combinations thereof. Preservatives, flavorings, and other additives such as, for example, anti-microbials, anti-oxidants, chelating agents, inert gases, and the like may also be present in a composition.

For oral administration, tablets or capsules can be prepared by conventional means with pharmaceutically acceptable excipients such as binding agents, fillers, lubricants, disintegrants, or wetting agents. The tablets can be coated by methods known in the art. Liquid preparations for oral administration can take the form of, for example, solutions, syrups or suspension, or can be presented as a dry product for constitution with saline or other suitable liquid vehicle before use. Liquid preparations also can contain pharmaceutically acceptable additives such as suspending agents, emulsifying agents, non-aqueous vehicles, preservatives, buffer salts, flavoring, coloring and sweetening agents as appropriate. Preparations for oral administration can be suitably formulated to give controlled release of the compound.

The invention further provides for an article of manufacture that includes a composition containing an active fraction of a Cimicifuga extract, and packaging material. The packaging material in or on an article of manufacture indicates that the composition therein is effective for reducing the level of an Aβ polypeptide. Components and methods for producing articles of manufactures are well known in the art. Instructions, for example on a label or package insert, describing a particular dose of the composition to be administered may be included in such kits. Different kits may be manufactured that contain a composition in different forms (e.g., a pill or a liquid) or that contain a dose of a composition appropriate to reduce the level of an Aβ polypeptide in, for example, an adult female subject or in an adult male subject (based upon an average weight). Instructions can further include a table or chart for adjusting a particular dose of a composition for a subject that deviates from average.

The invention will be further described in the following examples, which do not limit the scope of the invention described in the claims.

EXAMPLES

Example 1

Primary Screens to Identify Cimicifuga Extracts or Active Fractions thereof that Reduce the Level of an Aβ Polypeptide In Vitro Primary screens with cell cultures used a Cimicifuga ethanolic extract (obtained from Nature's Answer (www.naturesanswer.com) or Nature's Apothecary (Louisville, Colo.)). Nature's Answer provided ethanolic Cimicifuga extracts at 10–14% or 15–20%, while the Cimicifuga extract provided by Nature's Apothecary was at 55% ethanol. An appropriate dilution of each extract at a final concentration of 0.005%, 0.05% or 0.5% was placed into culture medium in a 96-well low binding microtiter library plate at the appropriate dilution. Vehicle controls, and 30 mM acetamidophenol were included in separate wells on each library plate to determine any vehicle-induced alterations in the level of Aβ, and for toxicity assessment, respectively (acetaminophen has been shown to be toxic to cells). The diluted Cimicifuga extracts and controls from the library plate were then directly placed onto confluent H4βAPP695 wt cells in a 96-well cell culture plate by multi-channel pipette. Following incubation for 12 hrs, the medium was removed by multi-channel pipette and aliquots immediately placed directly on 96-well sandwich ELISA plates for the measurement of Aβ40 or Aβ42 and on a 96-well LDH assay plate. The cells were then washed and subjected to a 96-well MTS assay.

In particular, the sandwich ELISA used herein was performed as follows: 96-well microtiter plates were coated overnight at 4° C. with 100 μl of a 5 μg/ml dilution of primary antibody in sodium carbonate coating buffer (SCCB; 0.1 M $Na_2CO_3$, pH 9.6). Plates were blocked overnight at 4° C. with 300 μl of Block Ace Solution (PBS+1.0% Block Ace (Snow Brand Milk Products, Japan), 0.05% $NaN_3$, pH 7.4). Samples for analysis and synthetic Aβ standards (Bachem, Switzerland) were diluted in buffer EC (0.02 M $NaH_2PO_4$, 0.002 M EDTA, 0.4 M NaCl, 0.2% BSA, 0.05% CHAPS, 0.04% Block Ace, 0.05% $NaN_3$, pH 7.0) and allowed to incubate on the plates overnight at 4° C. Plates were washed twice with PBS (8 mM $Na_2HPO_4$, 1.5 mM $KH_2PO_4$, 139 mM NaCl, 2.7 mM KCl, pH 7.4) and 100 μl of secondary antibody directly coupled to HRP (Pierce EZ-link Plus Activated Peroxidase kit, according to manufacturers directions; Pierce Chemical Co., Rockford, Ill.) was allowed to bind either 4 hrs at room temperature or overnight at 4° C. Plates were then washed twice with PBS containing 0.05% Tween 20 followed by two additional washes in PBS. Detection was performed using the TMB (3,3',5,5'-tetramethyl-benzidine) as an HRP substrate according to the manufacturer's specifications (Kirkegaard & Perry Laboratories (KPL), Gaithersburg, Md.) and the reaction stopped by the addition of 100 μl of 1N $H_3PO_4$. Plates were read at 450 nm in a SpectraMax Plus spectrophotometer (Molecular Devices; Sunnyvale, Calif.) and analyzed by SOFTmax® PRO software. Aβ40 or Aβ42 were quantitated by comparison with the values obtained for each synthetic Aβ standard from the same plate.

Example 2

Dose Response Analysis of C. racemosa Extract on the Level of Aβ40 and Aβ42 Polypeptides A statistically significant reduction in the level of Aβ42 was observed at all concentrations and with either C. racemosa extract examined. The specific effect on Aβ42 plateaued at approximately 50% inhibition. At concentrations greater than 0.15%, the level of Aβ40 also began to decrease in the presence of C. racemosa extract. The reduction in Aβ40 observed at the higher doses might be due to the presence of one or more other components within the extract that reduce either total Aβ or specifically Aβ40, or to overlapping effects on Aβ40 and Aβ42 by the same component.

Example 3

C. Racemosa Extract does not Significantly Affect the Accumulation of APP, Carboxyl Terminal Fragment α (CTFα) CTFβ, or sAPPα

APP, CTFβ and CTFα were analyzed in detergent-extracted cell lysates by Western blotting using an antibody directed against the last 20 amino acids of APP (provided by Dr. K. Sambamurti, Mayo Clinic, Jacksonville, Fla.). CTFβ is produced, along with sAPPβ, following β-secretase cleavage of APP, while CTFα and sAPPα are produced following cleavage of APP by α-secretase. sAPPα was detected in conditioned medium using the BAN-50 antibody against Aβ residues 1–16. The C. racemosa extract did not have a significant effect on the steady state levels of APP, CTFα, CTFβ, or sAPPα. Therefore, the effect of C. racemosa extract on Aβ42 was specific with respect to effects on APP processing.

Example 4

Multiple Lots of C. Racemosa Extract from Different Vendors Show Specific Reductions in Aβ42

To examine the uniformity of C. racemosa extract preparations, the variance between manufacturers' extracts was examined. H4βAPP695 wt cells were treated with C. racemosa ethanolic extracts obtained from 2 separate manufacturers (Nature's Answer, 10–14% or 15–20% ethanol; or Nature's Apothecary, 55% ethanol). Cells were treated with a final concentration of 0.1% of C. racemosa extract. C. racemosa extracts from each manufacturer showed a similar reduction in Aβ42.

Example 5

Secondary Screens Using Tg2576 Mice to Identify Extracts or Active Fractions Thereof that Reduce the Level of an Aβ Polypeptides In Vivo First, a dealcoholized extract or active fractions thereof are administered to young, aged matched, 4 week-old female Tg2576 mice. The effect of administration of an appropriate vehicle is used for control animals. Following a single administration of the test extract by gavage, the mice are sacrificed at defined time intervals and the brains analyzed for Aβ. 4 week-old mice are chosen so that Aβ is analyzed in the absence of any detectable deposition. 24 mice are assigned to a working dose group and the same number to a maximal dose group. For the working dose group, the dose of the extract given to the mice is equal to the body weight adjusted maximum dose reported for use in humans. For the maximal dose group, 250 μl is administered (i.e., the maximum volume that can be safely administered by gavage to mice of this age). 6 mice are sacrificed at each of 6, 12, 24 and 48 hrs post-administration. Plasma is obtained by conventional means from a terminal bleed and the brain is extracted and flash-frozen for analysis using the sandwich ELISA described herein. A significant reduction in Aβ42 is observed in the treated group when compared to the controls ($p<0.05$, Mann-Whitney).

Second, the extract or active fractions are administered for 2 wks to 4 week-old mice using the working dose and maximal dose as described above. 6 mice are treated per dose. As drug concentration approximates steady state in 4 half lives, this time course allows for steady state analysis of active components with half lives up to 3–4 days.

Third, mice are started dosing at 4 mo of age (prior to detectable deposition of Aβ) and are dosed for 10 mo until they reach 14 mo of age. This age is selected for sacrifice since it is one of the earliest periods where pathology is apparent and behavioral differences have been reported. 15 mice are assigned to each testing group. Controls animals receive vehicle alone. Mice are evaluated during the 10 mo period for behavioral changes and at the conclusion of the experiment, they are sacrificed to determine the extent of plaque formation, Aβ accumulation, and other neuropathology apparent in the Tg2576 mouse. One half of the brain is processed for Aβ quantitation by ELISA and one half is prepared for immunohistochemical analysis. *C. racemosa* extract treatment results in a significant reduction in Aβ42 in the older group of animals (p<0.05, Mann-Whitney).

The presence of abundant senile plaques throughout the hippocampus and neocortex is a pathological hallmark of Alzheimer's disease. A blinded immunohistochemical analysis is performed on both the control and drug-treated mice from the latter group to determine the effect of *C. racemosa* extract on senile plaque accumulation. *C. racemosa* extract treatment results in a significant reduction in the number of plaques as assessed using antibodies specific to Aβ. In adjacent sections, the majority of the immunoreactive plaques are also positive by thioflavin-S fluorescent microscopy. The total area occupied by these plaques is determined by image analysis of immunostained sections. A reduction in the area is observed in the drug-treated mice.

Example 6

Active Fractions of a *C. Racemosa* Extract

To assess the solubility and determine the molecular size of the active component in *C. racemosa* extract, a centrifugation and size exclusion experiment was performed. The activity of an ethanolic *C. racemosa* extract, soluble material following a 15,000 g spin, and the flow-through from a centrifugation using a filtration unit with a molecular weight cut-off of 10 kD were examined in cell cultures. These results indicated that the active component in *C. racemosa* extract was soluble and could pass through a 10 kD cut-off filter.

To examine the stability of the active component in *C. racemosa* extract, the extract was boiled for 5 min and then analyzed using the cell-based assay in a side-by-side comparison with non-boiled extract. Analysis of the boiled vs. non-boiled extract on H4βAPP695 cells showed an essentially equivalent reduction in the level of Aβ, demonstrating that an active component within a Cimicifuga extract is heat stabile.

Example 7

Bioassay-guided Identification and Isolation of an Active Component within *C. Racemosa* Extract An ethanolic *C. racemosa* extract was spun at 15,000 g to remove particulate material. The supernatant was lyophilized and re-suspended in distilled water. This suspension was then sequentially extracted in hexane, methylene dichloride, ethylacetate and n-butanol. The solvent extracts and the remaining water were aliquoted and rotovapped/lyophilized. An aliquot of each was resuspended in ethanol, diluted at several concentrations into H4 cell culture medium and analyzed for activity in the cell-based assays. Pure ethanol was diluted similarly as a control and the original extract diluted and analyzed in the cell-based assay to determine any substantial increase in activity. The methylene dichloride-soluble fraction, the ethyl acetate-soluble fraction, and the n-butanol-soluble fraction all demonstrated the ability to reduce the level of Aβ in the cell-based assay.

The solvent extract containing activity is then subject to preparative TLC followed by HPLC or HPLC directly as appropriate. HPLC fractions are then analyzed in the cell-based assay. The fraction with the highest activity is subjected to mass spectral, IR, and NMR analysis for structure identification. Additional separation steps as discussed herein can be included as necessary.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of reducing the level of a β-amyloid (Aβ) polypeptide in or secreted from a cell in vitro, said method comprising contacting said cell with an amount of a Cimicifuga extract or of an active fraction thereof effective for reducing the level of said Aβ polypeptide in or secreted from said cell and monitoring the level of said Aβ polypeptide in or secreted from said cell.

2. The method of claim 1, wherein said Cimicifuga extract or active fraction thereof is from *C. racemosa*.

3. The method of claim 2, wherein said *C. racemosa* extract or active fraction thereof is obtained from the root or rhizome of a *C. racemosa* plant.

4. The method of claim 2, wherein said *C. racemosa* extract is an ethanolic extract or an aqueous extract.

5. The method of claim 2, wherein an active component within said active fraction is soluble in a solvent selected from the group consisting of methylene dichloride, ethyl acetate and n-butanol.

6. The method of claim 5, wherein said active component is lipophilic.

7. The method of claim 2, wherein an active component within said active fraction has a molecular weight of less than 10 kD.

8. The method of claim 1, wherein said cell is selected from the group consisting of H4 cells, M17 cells, 293 cells, Chinese hamster ovary (CHO) cells, primary fibroblasts, C6, primary neuronal, primary mixed brain cultures, Daoy, SK-N-SH, SK-N-AS and SK-N-FI.

9. The method of claim 1, wherein said reduction in the level of said Aβ polypeptide is due to decreased production of said Aβ polypeptide or increased catabolism of said Aβ polypeptide.

10. The method of claim 1, wherein said level of said Aβ polypeptide is reduced by at least 10% compared to the level of said Aβ polypeptide in or secreted from a corresponding cell not contacted with said extract or active fraction thereof.

11. The method of claim 1, wherein said level of said Aβ polypeptide is reduced by at least 25% compared to the level of said Aβ polypeptide in or secreted from a corresponding cell not contacted with said extract or active fraction thereof.

12. The method of claim 1, wherein said level of said Aβ polypeptide is reduced by at least 50% compared to the level of said Aβ polypeptide in or secreted from a corresponding cell not contacted with said extract or active fraction thereof.

13. The method of claim 1, wherein said level of said Aβ polypeptide is reduced by at least 80% compared to the level of said Aβ polypeptide in or secreted from a corresponding cell not contacted with said extract or active fraction thereof.

14. The method of claim 1, wherein said Aβ polypeptide is Aβ40.

15. The method of claim 1, wherein said Aβ polypeptide is Aβ42.

16. The method of claim 1, wherein said reduction is preferential for Aβ42.

17. The method of claim 1, wherein said extract or active fraction thereof has no significant effect on the level of one or more of APP, CTFα, CTFβ, or sAPPα.

18. A method for reducing the level of an Aβ polypeptide in a mammal in need thereof, said method comprising administering an amount of a Cimicifuga extract or an active fraction thereof to said mammal effective for reducing the level of said Aβ polypeptide and monitoring the level of said Aβ polypeptide in said mammal.

19. The method of claim 18, wherein said extract or active fraction thereof is administered to said mammal orally, intravenously, intracranially, intracerebrally, subcutaneously, intramuscularly, intranasally or intraperitoneally.

20. The method of claim 18, wherein said mammal is a rodent.

21. The method of claim 20, wherein said rodent is a mouse.

22. The method of claim 21, wherein said mouse expresses an APP carrying a Swedish mutation.

23. The method of claim 22, wherein said mouse is a Tg2576 mouse.

* * * * *

UNITED STATES PATENT AND TRADEMARK OFFICE
CERTIFICATE OF CORRECTION

PATENT NO. : 6,649,196 B2
DATED : November 18, 2003
INVENTOR(S) : Christopher B. Eckman et al.

It is certified that error appears in the above-identified patent and that said Letters Patent is hereby corrected as shown below:

<u>Title page,</u>
Item [75], Inventors, "Sharie Haugabook", please delete "US" and insert -- Jamaica -- therefor; and "Abdul Fauq", please delete "US" and insert -- Pakistan -- therefor.

Signed and Sealed this

Thirtieth Day of March, 2004

JON W. DUDAS
*Acting Director of the United States Patent and Trademark Office*